United States Patent
Tobacman

(10) Patent No.: US 7,941,220 B2
(45) Date of Patent: May 10, 2011

(54) METHOD AND APPARATUS FOR MONITORING BATTERY STATUS OF IMPLANTABLE MEDICAL DEVICE

(75) Inventor: Kenneth Tobacman, Cedar, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 896 days.

(21) Appl. No.: 11/759,400

(22) Filed: Jun. 7, 2007

(65) Prior Publication Data

US 2008/0306569 A1 Dec. 11, 2008

(51) Int. Cl.
*A61N 1/08* (2006.01)
(52) U.S. Cl. .............................................. 607/29
(58) Field of Classification Search .............. 607/27, 607/29
See application file for complete search history.

(56) References Cited

U.S. PATENT DOCUMENTS

| 5,507,786 | A | 4/1996 | Morgan et al. |
| 5,722,999 | A | 3/1998 | Snell |
| 5,741,307 | A | 4/1998 | Kroll |
| 6,108,579 | A | 8/2000 | Snell et al. |
| 6,167,309 | A * | 12/2000 | Lyden ........................ 607/29 |
| 6,185,461 | B1 | 2/2001 | Er |
| 6,385,593 | B2 * | 5/2002 | Linberg ..................... 705/28 |
| 6,584,355 | B2 | 6/2003 | Stessman |
| 6,671,552 | B2 | 12/2003 | Merritt et al. |
| 6,901,293 | B2 | 5/2005 | Rogers et al. |
| 7,001,359 | B2 | 2/2006 | Rogers |
| 7,123,964 | B2 | 10/2006 | Betzold et al. |
| 7,194,308 | B2 | 3/2007 | Krig et al. |
| 2005/0007073 | A1 | 1/2005 | James et al. |
| 2005/0077872 | A1 | 4/2005 | Single |
| 2005/0102005 | A1 | 5/2005 | Krig et al. |
| 2005/0256548 | A1 | 11/2005 | Rogers et al. |

* cited by examiner

*Primary Examiner* — Carl H Layno
*Assistant Examiner* — Brian T Gedeon
(74) *Attorney, Agent, or Firm* — Schwegman, Lundberg & Woessner, P.A.

(57) ABSTRACT

A battery monitoring system monitors status of a battery in an implantable medical device by comparing a measured battery status trend to a calculated battery status trend. The measured battery status trend is a trend of measured parameter values each indicative of an actual state of depletion of the battery. The calculated battery status trend is a trend of calculated parameter values each indicative of an expected state of depletion of the battery.

26 Claims, 10 Drawing Sheets

METHOD AND APPARATUS FOR MONITORING BATTERY STATUS OF IMPLANTABLE MEDICAL DEVICE

TECHNICAL FIELD

This document relates generally to implantable medical devices and particularly to monitoring battery status of an implantable medical device.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. One particular example of implantable medical devices is a CRM device implanted in a patient to treat irregular or other abnormal cardiac rhythms by delivering electrical pulses to the patient's heart. Such rhythms result in diminished blood circulation. Examples of implantable CRM devices include pacemakers and defibrillators. Pacemakers are often used to treat patients with bradyarrhythmias, that is, hearts that beat too slowly or irregularly. Such pacemakers may coordinate atrial and ventricular contractions to improve the heart's pumping efficiency. Defibrillators are capable of delivering higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias, that is, hearts that beat too quickly. In addition to pacemakers and defibrillators, implantable CRM systems also include, among other things, pacer/defibrillators that combine the functions of pacemakers and defibrillators, drug delivery devices, and any other implantable systems or devices for diagnosing or treating cardiac arrhythmias.

Batteries are used as energy sources for implantable medical devices. While the use of battery allows a medical device to be totally implantable, without the need of transcutaneous power transmission, the power consumption and the longevity of the medical device is limited by the capacity of the battery. For example, most treatments using implantable CRM devices are long-term treatments that may last up to the patient's lifetime. When the battery of an implantable CRM device is no longer able to provide sufficient energy for the operation of the device, the device is to be explanted and replaced. Thus, for patient safety and device longevity, among other reasons, there is a need for monitoring the status of a battery in an implantable medical device.

SUMMARY

A battery monitoring system monitors the status of a battery in an implantable medical device by comparing a measured battery status trend to a calculated battery status trend. The measured battery status trend is a trend of measured parameter values each indicative of an actual state of depletion of the battery. The calculated battery status trend is a trend of calculated parameter values each indicative of an expected state of depletion of the battery.

In one embodiment, a system for monitoring status of a battery in an implantable medical device includes a battery analyzer. The battery analyzer includes a parameter input and a trending module. The parameter input receives measured values of a battery functional parameter and calculated values of the battery functional parameter. The battery functional parameter is indicative of a state of depletion of the battery. The measured values are each indicative of an actual state of depletion of the battery. The calculated values are each indicative of an expected state of depletion of the battery. The trending module produces a measured battery status trend being a trend of the measured values of the battery functional parameter and a calculated battery status trend being a trend of the calculated values of the battery functional parameter.

In one embodiment, a method for monitoring status of a battery in an implantable medical device is provided. Values of a battery functional parameter indicative of a state of depletion of the battery are measured. The measured values are each indicative of an actual state of depletion of the battery. Values of the battery functional parameter are each calculated as a function of one or more specification parameters of the battery and one or more consumption parameters indicative of energy consumption from the battery. The calculated values are each indicative of an expected state of depletion of the battery. A measured battery status trend being a trend of the measured values of the battery functional parameter and a calculated battery status trend being a trend of the calculated values of the battery functional parameter.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a battery monitoring system for monitoring status of a battery in an implantable medical device. The system measures values of a battery functional parameter, produces a measured battery status trend being a trend of the measured values of the battery functional parameter, calculates values of the battery functional parameter, and produces a calculated battery status trend being a trend of the calculated values of the battery functional parameter. The battery functional parameter is indicative of a state of depletion of the battery. Each measured value of the battery functional parameter is indicative of an actual state of depletion of the battery. Each calculated value of the battery functional parameter is indicative of an expected (or projected) state of depletion of the battery. The state of depletion of the battery is indicative of the remaining life of the battery. In various embodiments, one or more battery functional parameters are measured, calculated, and trended. In one embodiment, a measured battery status trend and a calculated battery status trend are produced for each battery functional parameter. In another embodiment, a measured battery status trend and a calculated battery status trend are produced for a parameter that is a function of a plurality of battery functional parameters.

The system monitors the depletion of the battery by using the measured battery status trend and the calculated battery status trend. In various embodiments, measured values of the battery functional parameters or values of the battery functional parameters taken from the measured battery status trend are compared to the calculated battery status trend. The difference between the actual state of depletion and the expected state of depletion is used to indicate, for example, adequacy of implantable medical device programming, performance of the implantable medical device, and/or remaining life of the battery (which in turn indicates a need to replace the implantable medical device).

Figure 1:
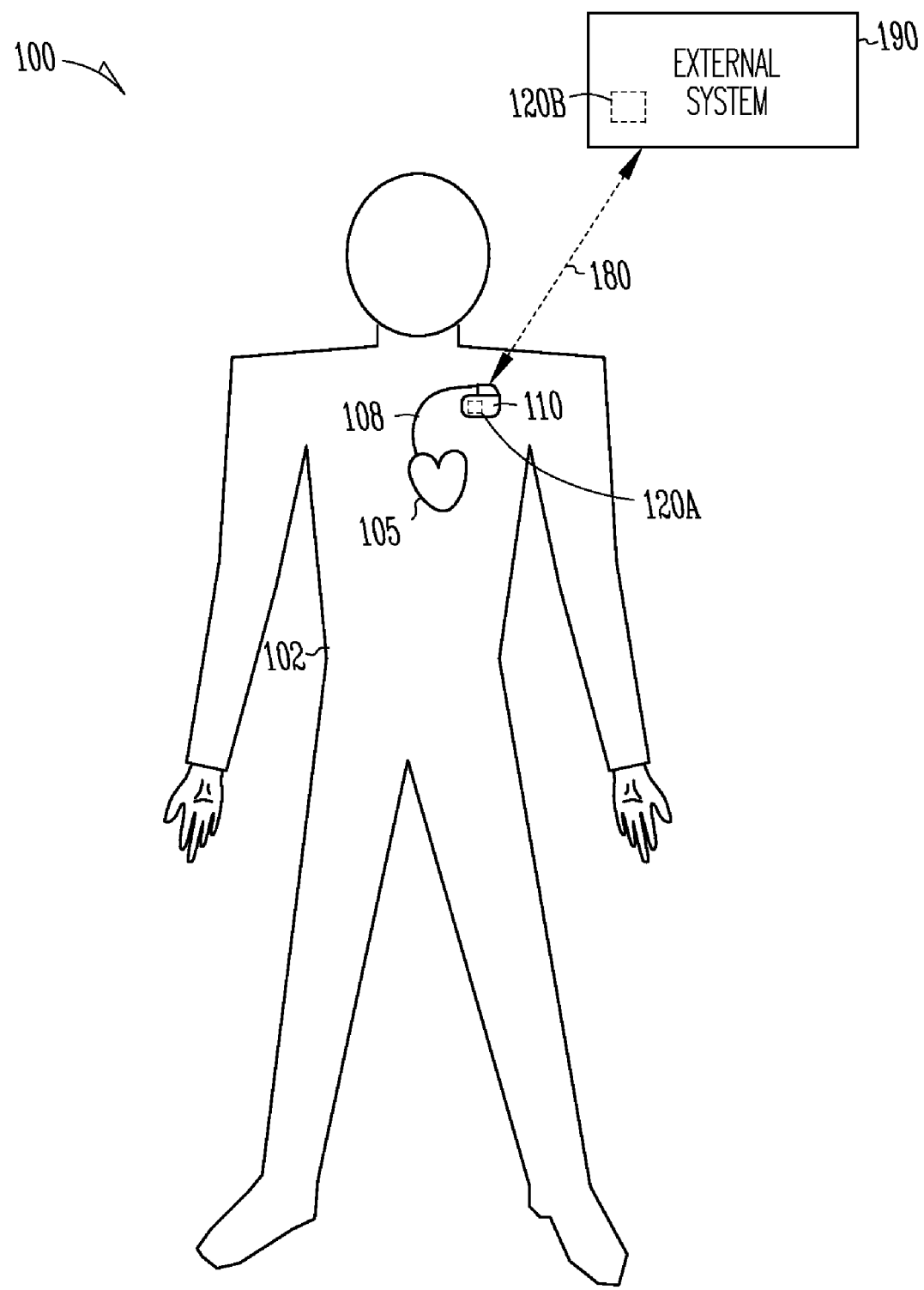
FIG. 1 is an illustration of an embodiment of a system including an implantable medical device and an external system and portions of an environment in which the system is used.

FIG. 1 is an illustration of an embodiment of a system 100 and portions of an environment in which system 100 is used. System 100 includes an implantable medical device 110, a lead system 108, and an external system 190. A wireless telemetry link 180 provides for communication between implantable medical device 110 and external system 190. Implantable medical device 110 is a battery-powered device. A battery monitoring system 120, including portions 120A in implantable medical device 110 and portions 120B in external system 190, provides implantable medical device 110 with battery monitoring. While a CRM system, as shown in FIG. 1, is discussed as a specific example, the present subject matter applies to any system that includes one or more battery-powered implantable medical devices.

After implantation, implantable medical device 110 operates within a body 102 of a patient to sense activities of a heart 105 and deliver one or more therapies to heart 105 through lead system 108. In one embodiment, as illustrated in FIG. 1, implantable medical device 110 is an implantable CRM device that delivers one or more therapies including, but are not limited to, a pacing therapy, a cardioversion/defibrillation therapy, a cardiac resynchronization therapy (CRT), a remodeling control therapy (RCT), a drug therapy, and a biological therapy such as a cell therapy and a gene therapy.

Lead system 108 provides one or more electrical connections between implantable medical device 110 and heart 105. In one embodiment, lead system 108 includes one ore more leads each including one or more electrodes configured for endocardial and/or epicardial placement. Pacing and/or cardioversion/defibrillation are delivered to heart 105 through such leads and electrodes. In one embodiment, one or more leads of lead system 108 also include agent delivery ports configured for endocardial, epicardial, and/or intravascular placement. Substances such as chemical or biological agents are delivered to heart 105 through such leads and agent delivery ports.

External system 190 communicates with implantable medical device 110 via telemetry link 180. In one embodiment, external system 190 includes an external programmner. In another embodiment, external system 190 includes a portable device, such as a hand-held device, provided for use by the patient or another person providing care to the patient. In another embodiment, external system 190 includes a patient management system including an external device communicating with implantable medical device 110 via telemetry link 180, a network coupled to the external device, and a remote device coupled to the network. Such a patient management system allows a physician or other caregiver to communicate with implantable medical device 110 through the remote device in a distant location.

Telemetry link 180 provides for data transmission between implantable medical device 110 and external system 190. Data transmission from implantable medical devices 110 to external system 190 includes, for example, transmitting real-time physiological data acquired by implantable medical devices 110, extracting physiological data acquired by and stored in implantable medical devices 110, extracting therapy history data stored in implantable medical devices 110, and extracting data indicating an operational status of implantable medical devices, such as battery status and lead impedance. Data transmission from external system 190 to implantable medical devices 110 includes, for example, programming implantable medical devices 110 to acquire physiological data, programming implantable medical devices 110 to perform at least one self-diagnostic test (such as for a battery status and lead impedance status), programming implantable medical devices 110 to perform a diagnostic task, and programming implantable medical devices 110 to deliver a therapy.

Battery monitoring system 120 monitors the status of one or more batteries in implantable medical device 110 by comparing the measured values of a battery functional parameter or a measured battery status trend to a corresponding calculated battery status trend to determine whether the actually state of depletion substantially deviates from a theoretically projected state of depletion. The result is used to indicate, for example, a need for reprogramming implantable medical device 110 to lower its power consumption and/or a need for replacing implantable medical device 110.

Figure 2:
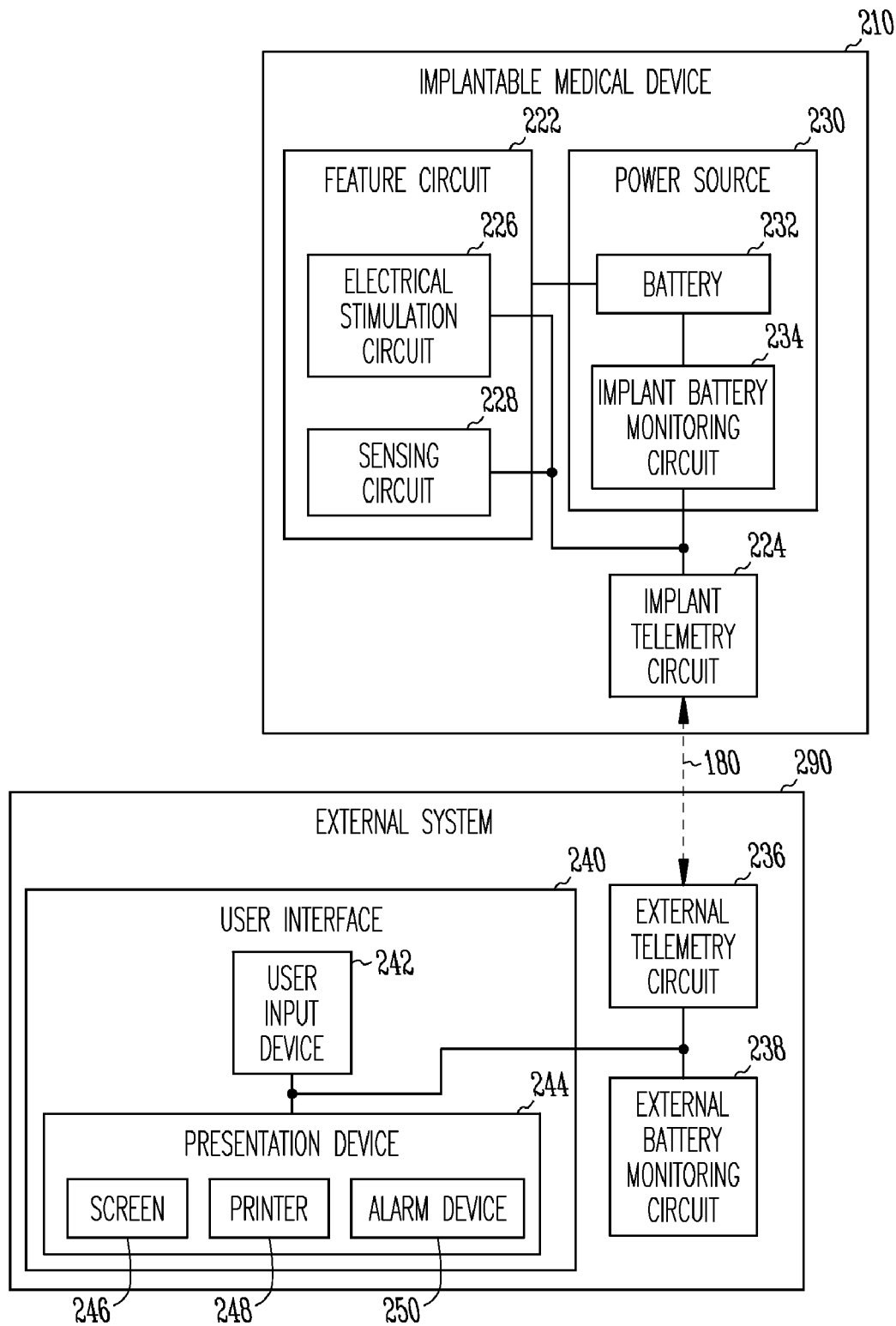
FIG. 2 is a block diagram illustrating an embodiment of circuits of the implantable medical device and the external system.

FIG. 2 is a block diagram illustrating an embodiment of circuits of an implantable medical device 210 and an external system 290. Implantable medical device 210 represents an embodiment of implantable medical device 110 and includes a feature circuit 222, an implant telemetry circuit 224, and a power source 230. External system 290 represents an embodiment of external system 190 and includes an external telemetry circuit 236, an external battery monitoring circuit 238, and a user interface 240. Telemetry link 180 provides for data transmission between implantable medical device 210 and external system 290.

Feature circuit 222 performs one or more of sensing, diagnostic, and therapeutic functions. In one embodiment, as illustrated in FIG. 2, feature circuit 222 includes an electrical stimulation circuit 226 and a sensing circuit 228. Electrical stimulation circuit 226 delivers electrical stimulation to body 102. Examples of electrical stimulation circuit 226 include a pacing circuit that delivers pacing pulses, a cardioversion/defibrillation circuit that delivers cardioversion/defibrillation pulses, and a neural stimulation circuit that delivers neural stimulation pulses. Sensing circuit 228 senses one or more physiological signals such as electrograms, heart sounds or signals indicative of heart sounds, activity level signals, pressure signals, impedance signals, and respiratory signals. In various embodiments, feature circuit 222 includes one or more of electrical stimulation circuit 226, sensing circuit 228, a diagnostic circuit to perform one or more diagnostic functions using the one or more physiological signals sensed by sensing circuit 228, a drug delivery device to deliver one or more pharmaceutical agents, and a biological therapy device to deliver one or more biologic therapies.

Power source 230 includes a battery 232 and an implant battery monitoring circuit 234. Battery 232 represents one or more batteries housed in implantable medical device 210 to provide energy for its operation, including energy delivered to body 102 for therapeutic purposes. Examples of battery 232 include lithium manganese dioxide and lithium carbon monofluoride batteries. In one embodiment, battery 232 includes one or more rechargeable batteries such as rechargeable lithium and lithium ion batteries, in addition to or in place of one or more non-rechargeable batteries.

Implant telemetry circuit 224 receives signals from external system 290 and transmits signals to external system 290 via telemetry link 180. In one embodiment, implant telemetry circuit 224 also allows for communication between implantable medial device 210 and one or more other implantable medical devices implanted in body 102. External telemetry circuit 236 transmits signals to implantable medial device 210 and receives signals transmitted from implantable medical device 210 via telemetry link 180.

Implant battery monitoring circuit 234 and external battery monitoring circuit 238 include battery monitoring system 120. In various embodiments, components of battery monitoring system 120 are distributed in implantable medical device 210 and external system 290. Examples of this distribution are discussed below, with reference to FIGS. 7 and 8.

User interface 240 allows a user such as the physician or other caregiver or the patient to communicate with implantable medical device 210. User interface 240 includes a user input device 242 and a presentation device 244. User input device 242 receives information such as commands and parameters from the user. Presentation device 244 informs the user of the status of the patient, implantable medical device 210, and external system 290. In the illustrated embodiment, presentation device 244 includes a screen 246, a printer 248, and an alarm device 250. For example, information representative of the status of battery 232 acquired by battery monitoring system 120, including the measured and calculated battery status trends, are displayed on screen 246 and/or printed on printer 248. If battery monitoring system 120 detects an alerting event, such as an abnormally high power consumption or low energy level indicating a need for battery replacement, alarm device 250 produces an alarm signal such as an audio tone or a textual message. In response, the user determines whether there is a need to replace implantable medical device 210 or to reprogram therapy parameters used by feature circuit 222. For example, abnormally high power consumption may be caused by inappropriate device setting or higher-than expected use of therapeutic energy due to physiology of a particular patient. In such cases, the power consumption may be lowered by reprogramming implantable medical device 210 with adequate therapy parameters and/or an alternative therapy strategy. On the other hand, an abnormally high power consumption caused by device failure usually requires replacement of implantable medical device 210.

Figure 3:
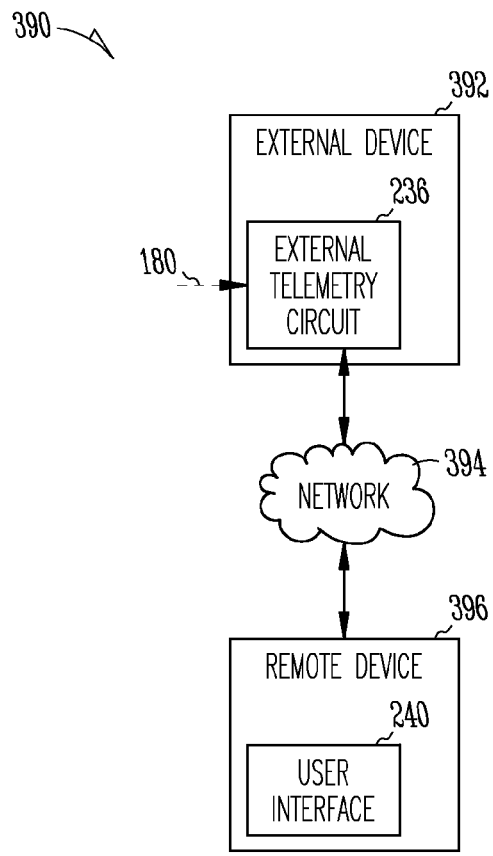
FIG. 3 is a block diagram illustrating an embodiment of the external system.

FIG. 3 is a block diagram illustrating an embodiment of an external system 390, which represents an embodiment of the distribution of external system 190. As illustrated in FIG. 3, external system 390 is a patient management system including an external device 392, a telecommunication network 394, and a remote device 396. External device 394 is placed within the vicinity of implantable medical device 190 and includes external telemetry circuit 236 to communicate with implantable medical device 190 via telemetry link 180. Remote device 396 is in a remote location and communicates with external device 392 through network 394, thus allowing the user to monitor and treat a patient from a distant location and/or allowing access to various treatment resources from the remote location. Remote device 396 includes user interface 240, or at least a portion of user interface 240, and allows the user to monitor the battery of implantable medical device 110 through battery monitoring system 120. In one embodiment, external system 390 allows for monitoring of batteries in multiple implantable medical devices, including statistical analysis using data acquired from multiple implantable medical devices to indicate battery usage and performance in these devices.

Figure 4:
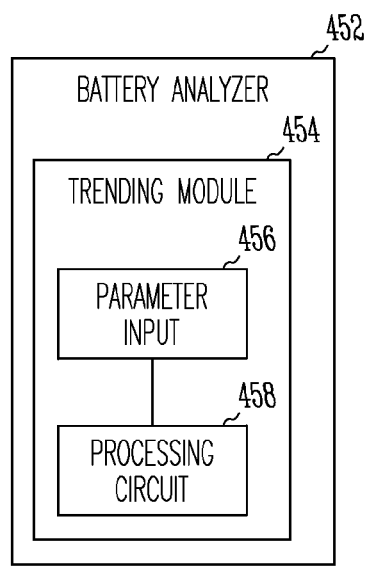
FIG. 4 is a block diagram illustrating an embodiment of a battery analyzer.

FIG. 4 is a block diagram illustrating an embodiment of a battery analyzer 452 of battery monitoring system 120. Battery analyzer 452 includes a trending module 454. Trending module 454 includes a parameter input 456 and a processing circuit 458. Parameter input 456 receives measured values of a battery functional parameter and calculated values of the battery functional parameter. The battery functional parameter indicates the remaining energy in a battery relative to the full capacity of the battery. The measured values are each measured from battery 232 and each indicate an actual state of depletion of battery 232. The calculated values are each calculated using a predetermined formula with known parameters such as battery specification parameters and therapy energy consumption and each indicate an expected state of depletion of battery 232. Processing circuit 458 produces a measured battery status trend and a calculated battery status trend. The measured battery status trend is a trend of the measured values of the battery functional parameter. The calculated battery status trend is a trend of the calculated values of the battery functional parameter.

In various embodiments, instructions for producing the measured battery status trend and the calculated battery status trend are stored in a storage device coupled to or included in processing circuit 458 and in a form that is readable and executable by processing circuit 458. In one embodiment, processing circuit 458 includes portions of a microprocessor, such as a microprocessor of implantable medical device 110 or 210, configured to execute the instructions for producing the measured battery status trend and the calculated battery status trend. In another embodiment, processing circuit 458 includes portions of a microprocessor or other processing circuit of a computer or computerized device, such as a computer or computerized device of external system 190 or 290, configured to execute instructions for producing the measured battery status trend and the calculated battery status trend.

Figure 5:
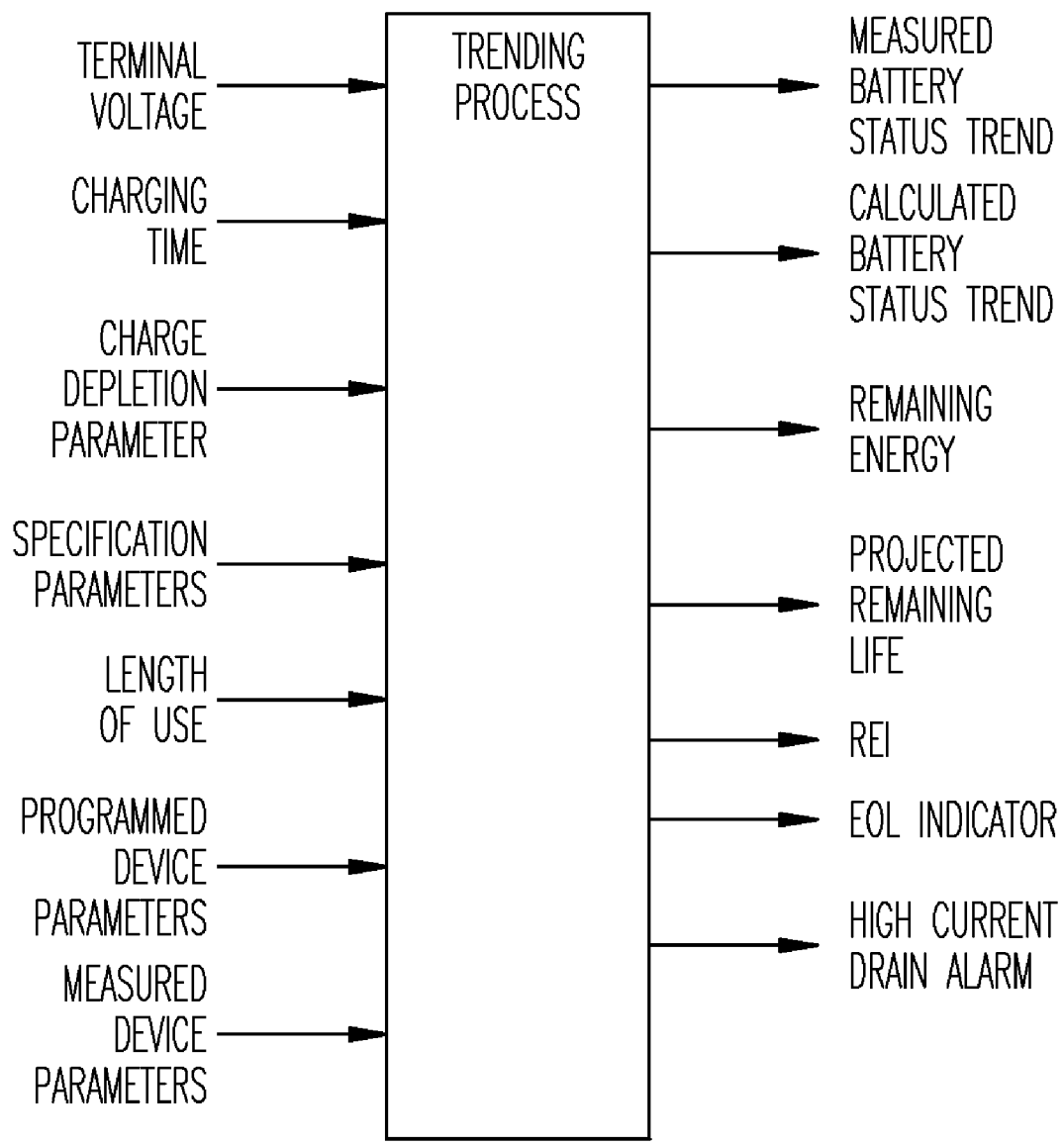
FIG. 5 is an illustration of an embodiment of a trending process showing its inputs and outputs.

FIG. 5 is an illustration of an embodiment of a trending process showing its inputs and outputs. In one embodiment, the trending process is performed using processing circuit 458 for a battery in an implantable medical device. In the illustrated embodiment, the inputs include a terminal voltage being a voltage across two terminals of the battery, a charging time being a time interval during which a capacitor in the implantable medical device (such as a defibrillation capacitor) is charged to a specified energy level using the battery, a charge depletion parameter indicative of a cumulative charge depleted from the battery, specification parameters ("factory parameters") of the battery, length of use (i.e., length of time since implantation of the implantable medical device), programmed device parameters of the implantable medical device, and measured device parameters of the implantable medical device. The outputs include the measured and the calculated battery status trends and parameters and indicators derived from these trends, including the remaining energy of the battery, a projected remaining life of the battery, an elective replacement indicator (ERI), an end-of-life (EOL) indicator, and a high current drain alarm signal. In various embodiments, the inputs of the trending process include any one or more inputs selected from those illustrated in FIG. 5 and additional inputs suitable for use in the battery status trending, and the outputs of trending process include any one or more outputs selected from those illustrated in FIG. 5 and additional outputs for battery monitoring. An example of a system that performs the trending process is further discussed below, with reference to FIG. 7.

Figure 6:
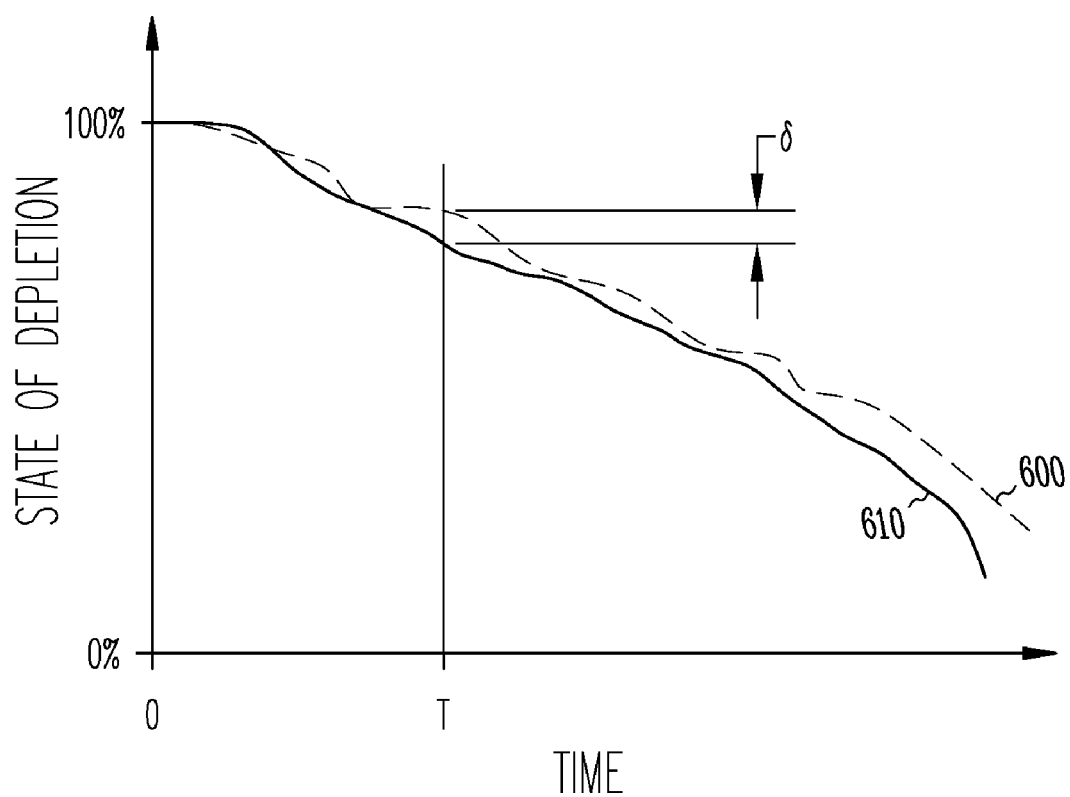
FIG. 6 is a graph illustrating a measured battery status trend and a calculated battery status trend.

FIG. 6 is a graph illustrating a measured battery status trend 610 and a calculated battery status trend 600. Measured battery status trend 610 represents a specific example for the measured battery status trend produced by processing circuit 458. Calculated battery status trend 600 represents a specific example of the calculated battery status trend produced by processing circuit 458. The state of depletion is represented by the remaining capacity of battery 232 as a percentage the full capacity of battery 232. As illustrated in FIG. 6, measured battery status trend 610 deviates from calculated battery status trend 600 by a difference δ. In various embodiments, the difference δ is used as an indication of whether the usage and performance of battery 232 is within a normal range. A difference δ that is outside the normal range indicates a need for user intervention, such as to preserve the longevity of implantable medical device 110. Additionally, measured battery status trend 610 and calculated battery status trend 600 provide for an indication when battery 232 is near its end of life, which requires replacement of implantable medical device 110.

Figure 7:
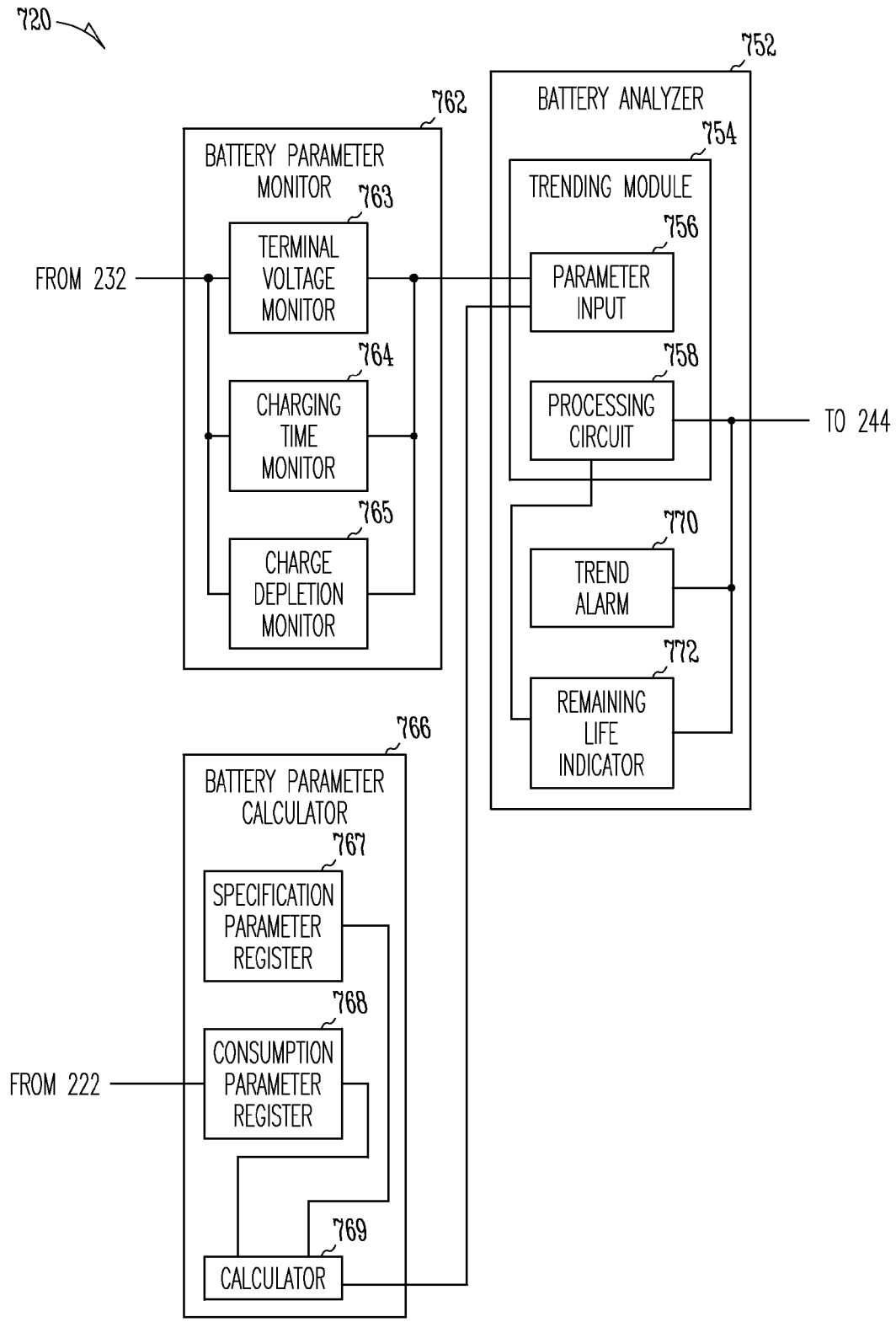
FIG. 7 is a block diagram illustrating an embodiment of a battery monitoring system including the battery analyzer.

FIG. 7 is a block diagram illustrating an embodiment of a battery monitoring system 720, which represents an embodiment of battery monitoring system 120. Battery monitoring system 720 includes a battery parameter monitor 762, a battery parameter calculator 766, and a battery analyzer 752. In the illustrated embodiment, battery monitoring system 720 includes a trending module and its peripheral devices to perform the trending process discussed above with reference to FIG. 5.

Battery parameter monitor 762 measures the values of one or more battery functional parameters indicative of the state of depletion of battery 232. In the illustrated embodiment, battery parameter monitor 762 includes a terminal voltage monitor 763, a charging time monitor 764, and a charge depletion monitor 765. In various other embodiments, battery parameter monitor 762 includes any one or more of terminal voltage monitor 763, charging time monitor 764, and charge depletion monitor 765, depending on the battery functional parameter(s) selected for trending. Terminal voltage monitor 763 measures a terminal voltage being the voltage across two terminals of battery 232. Charging time monitor 764 measures a capacitor charging time being a time interval during which a capacitor in implantable medical device 110 (such as a defibrillation capacitor) is charged to a specified energy level using battery 232. Charge depletion monitor 765 measures a charge depletion parameter indicative of a cumulative charge depleted from battery 232. An example of measuring the charge depletion parameter is discussed in U.S. patent application Ser. No. 10/706,856, entitled "SYSTEM AND METHOD FOR MONITORING OR REPORTING BATTERY STATUS OF IMPLANTABLE MEDICAL DEVICE", filed on Nov. 12, 2003, assigned to Cardiac Pacemakers, Inc., which is incorporated herein by reference in its entirety.

Battery parameter calculator 766 calculates the value of the one or more battery functional parameters and includes a specification parameter register 767, a consumption parameter register 768, and a calculator 769. Specification parameter register 767 stores specification parameters including the "factory parameters" specified for battery 232. Consumption parameter input 768 receives and stores consumption parameters including various parameters indicative of or contributing to the energy consumed from battery 232. Calculator 769 produces the values of the battery functional parameter each as a function of one or more specification parameters and one or more consumption parameters. The calculated values each represent a theoretical expectation for the state of depletion of battery 232 based on the built-in characteristics of battery 232 and how it is expected to be used. An example of a specification parameter includes the battery capacity specified for battery 232. Examples of the consumption parameters include the length of time since implantation of implantable medical device 110, programmed device parameters such as parameters controlling delivery of therapeutic energy from implantable medical device 110 (such as programmed pacing and defibrillation parameters), measured device parameters (such as impedance of each lead in lead system 108), and operation history parameters indicative of energy consumed from battery 232 (such as number of defibrillation shocks delivered since device implantation).

Battery analyzer 752 is a specific embodiment of battery analyzer 452 and includes a trending module 754, a trend alarm 770, and a remaining life indicator 772. Trending module 754 includes a parameter input 756 and a processing circuit 758. Parameter input 756 receives parameters including the inputs to processing circuit 758. Processing circuit 758 represents an embodiment of processing circuit 458 and produces the measured battery status trend and the calculated battery status trend using the parameters received by parameter 554. In one embodiment, processing circuit 758 produces a measured battery status trend and a corresponding calculated battery status trend for one battery functional parameter. In another embodiment, processing circuit 758 produces a measured battery status trend and a corresponding calculated battery status trend for each of a plurality of battery functional parameters. In another embodiment, processing circuit 758 produces a measured battery status trend and a corresponding calculated battery status trend for a battery parameter being a function of a plurality of battery functional parameters. In one embodiment, trending module 754 updates the measured battery status trend and the calculated battery status trend periodically, such as on a daily basis. This includes receiving the currently measured values of the battery functional parameter, receiving the currently calculated values of the battery functional parameter, updating the measured battery status trend, and updating the calculated battery status trend on the period basis. The measured battery status trend and the calculated battery status trend are presented using presentation device 244 periodically or upon request by the user.

Trend alarm 770 produces an alert signal using the measured battery status trend and the calculated battery status trend, or using a rate of change in the measured battery status trend and a rate of change in the calculated battery status trend. In one embodiment, trend alarm 770 produces the alert signal when the measured battery status trend deviates from the calculated battery status trend by at least a specified performance margin (i.e., when δ exceeds the predetermined performance margin) for a monitoring period. In another embodiment, trend alarm 770 produces the alert signal when a derivative of the measured battery status trend deviates from a derivative of the calculated battery status trend by at least a specified performance rate margin for the monitoring period. Remaining life indicator 772 produces the battery life parameter using the measured battery status trend and the calculated battery status trend. The measured battery status trend indicates the battery usage in the past, and the calculated battery status trend indicates projected battery usage in the future. In one embodiment, remaining life indicator produces the ERI and/or the EOL indicator for battery 232 using the battery life parameter. Such indicators are presented using presentation device 244 to inform the use of the need for replacement of battery 232 (typically requiring replacement of implantable medical device 110 that is powered by battery 232).

Figure 8:
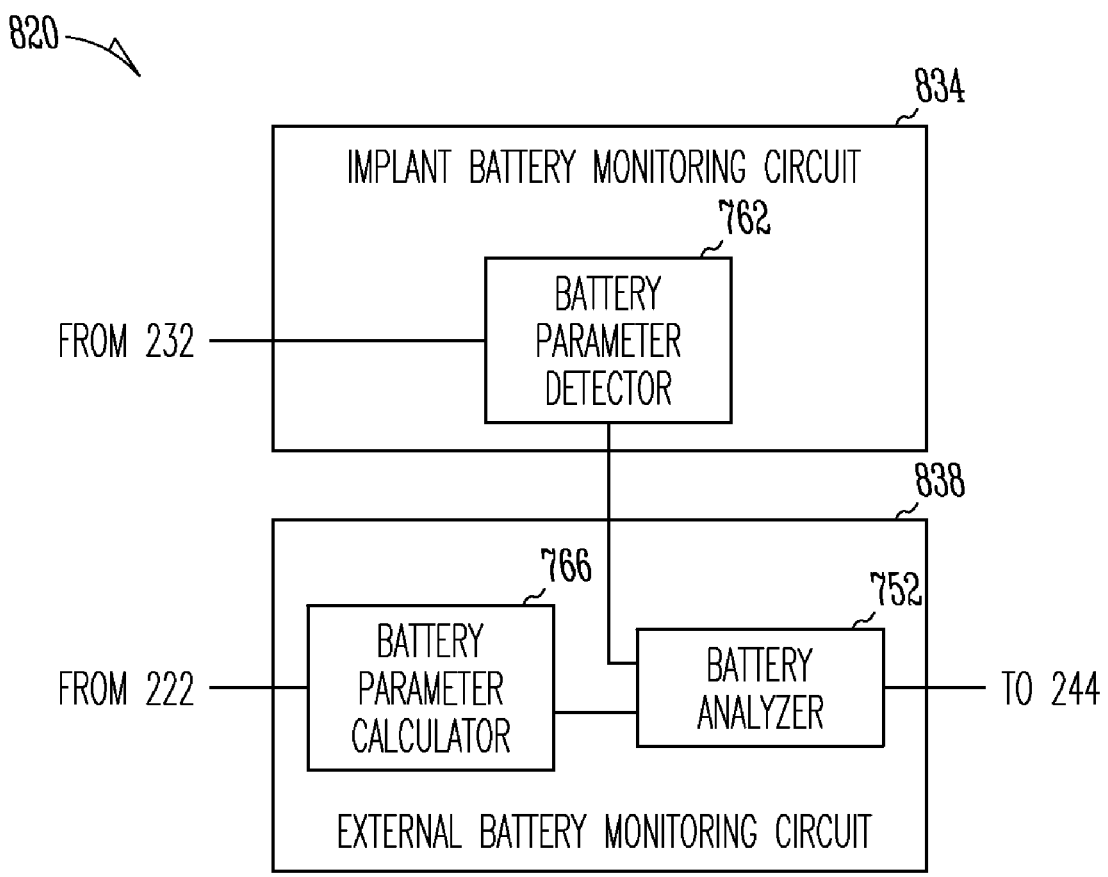
FIG. 8 is a block diagram illustrating an embodiment of distribution of the battery monitoring system in the implantable medical device and the external system.

FIG. 8 is a block diagram illustrating an embodiment of a battery monitoring system 820, which represents an embodiment of distribution of battery monitoring system 720 in an implant medical device and an external system. An implant battery monitoring circuit 834 represents an embodiment of implant battery monitoring circuit 234 and includes battery parameter monitor 762. An external battery monitoring circuit 838 represents an embodiment of external battery monitoring circuit 238 and includes battery parameter calculator 766 and battery analyzer 752.

Battery monitoring system 820 allows for analysis of battery status using information from a plurality of implantable medical devices. In one embodiment, parameter input 456 receives the measured and/or calculated values of the battery functional parameter for a plurality of implantable medical devices. Battery parameter calculator 766 adjusts the calculated value of the battery functional parameter using the measured and/or calculated values of the battery functional parameter from the plurality of implantable medical devices. Trend alarm 770 produces the specified performance margin using the measured and/or calculated values of the plurality of implantable medical devices. Remaining life indicator 772 calculates the battery life parameter for each of the implantable medical devices using the measured and/or calculated values of the plurality of implantable medical devices.

Figure 9:
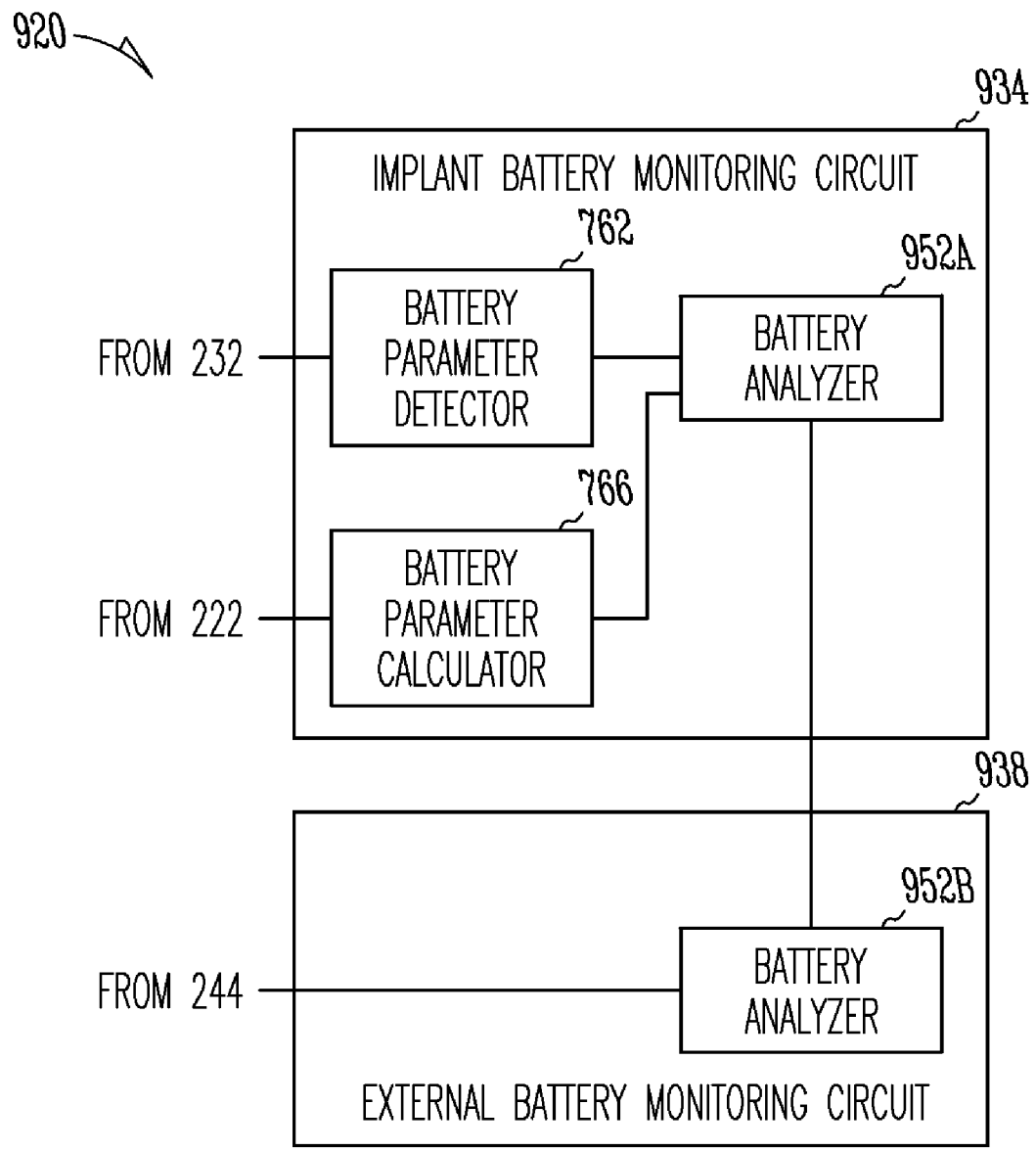
FIG. 9 is a block diagram illustrating another embodiment of distribution of the battery monitoring system in the implantable medical device and the external system.

FIG. 9 is a block diagram illustrating an embodiment of a battery monitoring system 920, which represents another embodiment of distribution of battery monitoring system 720 in an implant medical device and an external system. An implant battery monitoring circuit 934 represents another embodiment of implant battery monitoring circuit 234 and includes battery parameter monitor 762, battery parameter calculator 766, and a battery analyzer 952A. An external battery monitoring circuit 938 represents another embodiment of external battery monitoring circuit 238 and includes a battery analyzer 952B. Battery analyzer 952A represents portions of battery analyzer 752 distributed in the implantable medical device. Battery analyzer 952B represents portions of battery analyzer 752 distributed in the external system. Battery monitoring system 920 allows for battery status monitoring while communication between the implantable medical device and the external system is not established.

Figure 10:
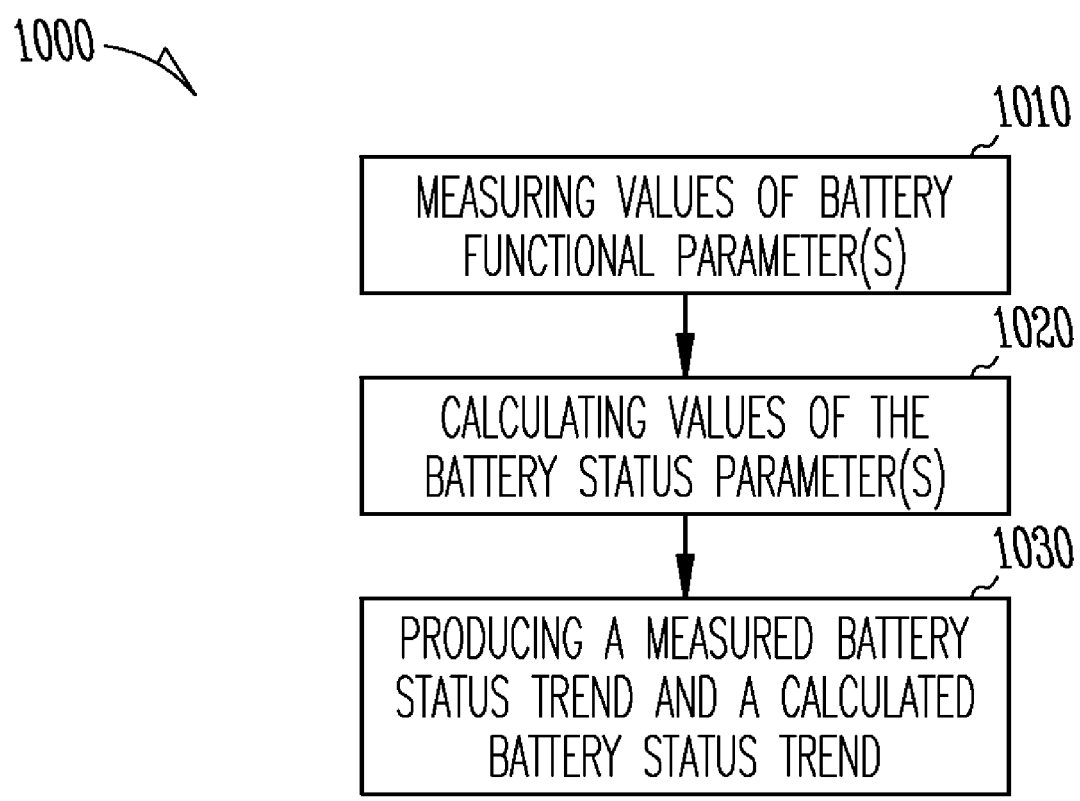
FIG. 10 is a flow chart illustrating an embodiment of a method for monitoring status of a battery in an implantable medical device.

FIG. 10 is a flow chart illustrating an embodiment of a method 1000 for monitoring status of a battery in an implantable medical device. In one embodiment, method 1000 is performed by system 100, including its various embodiments discussed above.

Values of one or more battery functional parameters are measured at 1010. The battery functional parameter is indicative of a state of depletion of the battery. The measured values are each indicative of an actual state of depletion of the battery. Examples of the one or more battery functional parameters include a terminal voltage being a voltage across two terminals of the battery, a capacitor charging time being a time interval during which a capacitor in the implantable medical device is charged to a specified energy level using the battery, and a charge depletion parameter indicative of a cumulative charge depleted from the battery. An example of measuring the charge depletion parameter is discussed in U.S. patent application Ser. No. 10/706,856.

Values of the one or more battery functional parameter are calculated at 1020. The calculated values are each indicative of an expected state of depletion of the battery and is a function of one or more specification parameters of the battery and one or more parameters indicative of energy consumption from the battery. In various embodiments, the calculated values of the one or more battery functional parameters are produced using parameters such as battery capacity, length of time since implantation of the implantable medical device, programmed and/or measured device parameters affecting the energy consumption from the battery, measured device parameters, and/or operation history parameters indicative of energy consumed from the battery. In one embodiment, the values of the one or more battery functional parameter is calculated at 1020 as a function of one or more specification parameters of the battery, one or more parameters indicative of energy consumption from the battery, and the measured and/or calculated values of the battery functional parameter for a plurality of implantable medical devices.

A measured battery status trend and a calculated battery status trend are produced at 1030. The measured battery status trend is a trend of the measured values of the one or more battery functional parameters. The calculated battery status trend is a trend of the calculated values of the one or more battery functional parameters. In one embodiment, the measured and calculated battery status trends are updated periodically, such as on a daily basis. The measured battery status trend and the calculated battery status trend are presented to a user such as a physician or other caregiver using a screen or printer. In various embodiments, one or more of the terminal voltage, the capacitor charging time, and the charge depletion parameter are measured at 1010, calculated at 1020, and trended at 1030.

Figure 11:
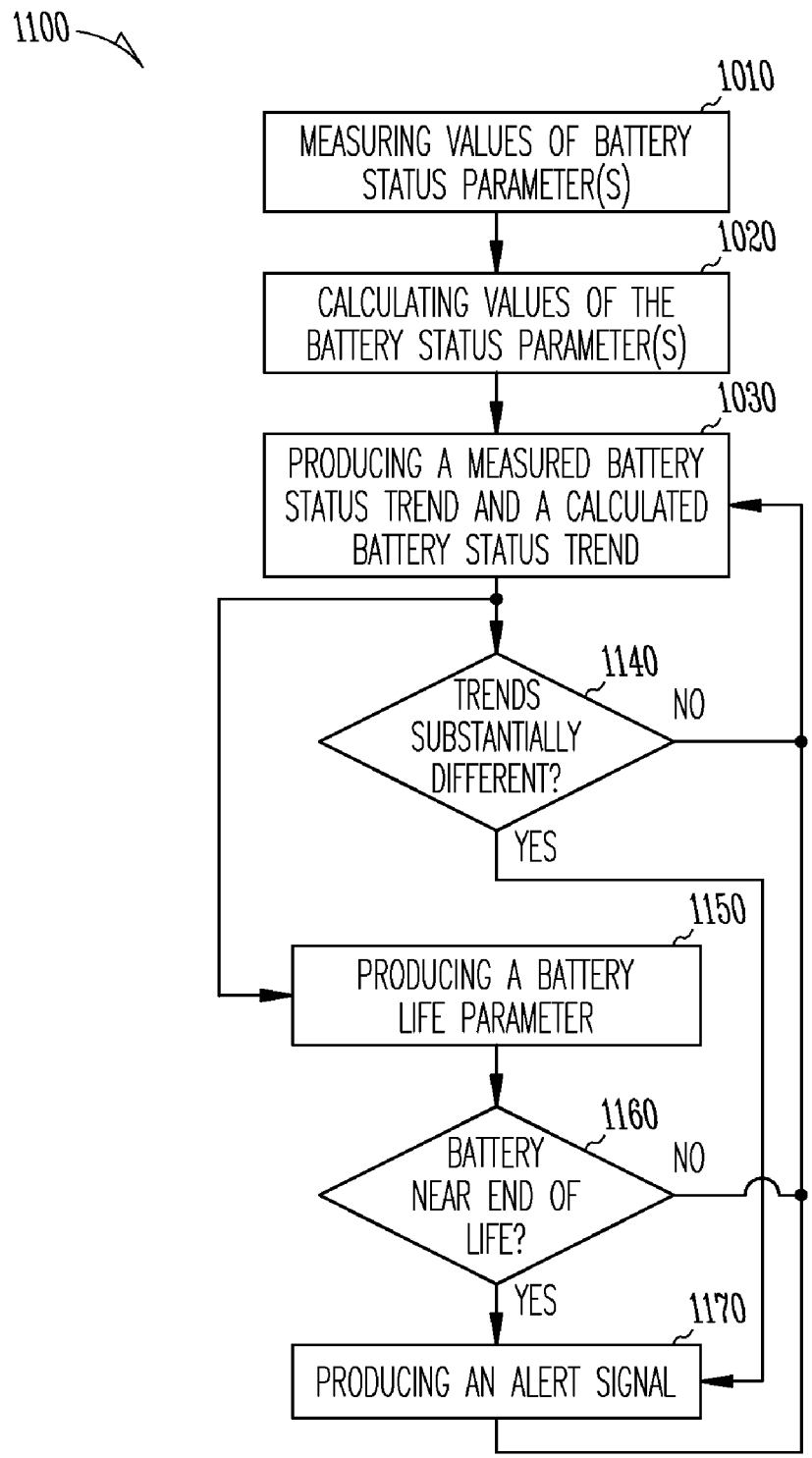
FIG. 11 is a flow chart illustrating another embodiment of a method for monitoring status of the battery in the implantable medical device.

FIG. 11 is a flow chart illustrating an embodiment of a method 1100, which represents a further embodiment of method 1000. In one embodiment, method 1100 is performed by system 100, including its various embodiments discussed above. Method 1100 starts with method 1000. That is, values of one or more battery functional parameter are measured at 1010, values of the one or more battery functional parameter are calculated at 1020, and a measured battery status trend and a calculated battery status trend are produced at 1030.

If the measured battery status trend is substantially different from the calculated battery status trend at 1140, an alert signal is produced at 1170. In one embodiment, the alert signal is produced at 1140 when the measured battery status trend deviates from the calculated battery status trend by at least a specified performance margin for a monitoring period. In another embodiment, the alert signal is produced at 1140 when a derivative of the measured battery status trend deviates from a derivative of the calculated battery status trend by at least a specified performance rate margin for the monitoring period. In one embodiment, in response to the alert signal, an alarm signal, such as an audio tone, a visual warning signal, or a textual message, is produced to notify the user. In one embodiment, the performance margin is adjusted using the measured and/or calculated values of the battery functional parameter for the plurality of implantable medical devices.

A battery life parameter is produced at 1150, using the measured battery status trend and the calculated battery status trend. The battery life parameter represents an estimated remaining life expectancy of the battery. In one embodiment, the battery life parameter is produced for the implantable medical device using the measured and/or calculated values of the battery functional parameter for the plurality of implantable medical devices. If the battery life parameter indicates that the battery is near its end of life at 1160, the alert signal is produced at 1170 to notify the user. In one embodiment, this includes generating an ERI and/or an EOL using the battery life parameter to present to the user.

It is to be understood that the above detailed description is intended to be illustrative, and not restrictive. The scope of the invention should, therefore, be determined with reference to the appended claims, along with the full scope of equivalents to which such claims are entitled.

What is claimed is:

1. A system for monitoring status of a battery in an implantable medical device, the system comprising:
   a battery analyzer configured to analyze the status of the battery, the battery analyzer including a trending module including:
      a parameter input configured to receive measured values of a battery functional parameter and calculated values of the battery functional parameter, the battery functional parameter indicative of a state of depletion of the battery and including at least a terminal voltage being a voltage across terminals of the battery, the measured values each indicative of an actual state of depletion of the battery, the calculated values each indicative of an expected state of depletion of the battery; and
      a processing circuit configured to produce a measured battery status trend being a trend of the measured values of the battery functional parameter and a calculated battery status trend being a trend of the calculated values of the battery functional parameter.

2. The system of claim 1, wherein the trending module is configured to update the measured battery status trend and the calculated battery status trend on a periodic basis.

3. The system of claim 1, wherein the battery analyzer comprises a trend alarm coupled to the trending module and configured to produce an alert signal when the measured battery status trend deviates from the calculated battery status trend by at least a specified performance margin for a monitoring period.

4. The system of claim 3, wherein the trend alarm is configured to produce the alert signal when a rate of change of the measured battery status trend deviates from a rate of change of the calculated battery status trend by at least a specified performance rate margin for the monitoring period.

5. The system of claim 1, wherein the battery analyzer comprises a remaining life indicator coupled to the trending module and configured to produce a battery life parameter representing an estimated remaining life expectancy of the battery using the measured battery status trend and the calculated battery status trend.

6. The system of claim 1, comprising:
   a battery parameter monitor configured to measure the battery functional parameter and produce the measured values of the battery functional parameter, the battery parameter monitor including at least a terminal voltage monitor configured to measure the terminal voltage; and
   a battery parameter calculator configured to produce the calculated values of the battery functional parameter each as a function of one or more specification parameters of the battery and one or more consumption parameters indicative of energy consumption from the battery.

7. The system of claim 6, wherein the battery parameter monitor further comprises a charging time monitor configured to measure a capacitor charging time being a time interval during which a capacitor in the implantable medical device is charged to a specified energy level using the battery.

8. The system of claim 6, wherein the battery parameter monitor further comprises a charge depletion monitor configured to produce a charge depletion parameter indicative of a cumulative charge depleted from the battery.

9. The system of claim 6, wherein the battery parameter calculator is configured to calculate the values of the battery functional parameter each as a function of one or more of a specified battery capacity, a length of time since implantation of the implantable medical device, stimulation parameters affecting the energy consumption from the battery, and operation history parameters indicative of energy consumed from the battery.

10. The system of claim 6, wherein the implantable medical device comprises an implant battery monitoring circuit coupled to the battery, and further comprising an external system communicatively coupled to the implantable medical device and including an external battery monitoring circuit, wherein one or more of the implant battery monitoring circuit and the external battery monitoring circuit include the battery analyzer.

11. The system of claim 10, wherein the external system comprises a presentation device configured to present the measured battery status trend and the calculated battery status trend.

12. The system of claim 11, wherein the presentation device comprises a screen adapted to display one or more of the measured battery status trend and the calculated battery status trend.

13. The system of claim 11, wherein the presentation device comprises a printer adapted to print one or more of the measured battery status trend and the calculated battery status trend.

14. The system of claim 11, wherein the presentation device comprises an alarm device adapted to produce an alarm signal indicative of a need for battery replacement.

15. The system of claim 10, wherein the implant battery monitoring circuit comprises the battery parameter monitor, the battery parameter calculator, and portions of the battery analyzer.

16. The system of claim 10, wherein the implant battery monitoring circuit comprises the battery parameter monitor, and the external battery monitoring circuit comprises the battery parameter calculator and the battery analyzer.

17. The system of claim 16, wherein the external battery monitoring circuit is configured to receive the measured values of the battery functional parameter from each of a plurality of other implantable medical devices, and the battery analyzer is programmed to analyze the status of the battery using the measured and calculated values of the battery functional parameter from the plurality of other implantable medical devices.

18. The system of claim 10, wherein the external system comprises an external device communicatively coupled to the implantable medical device via a telemetry link, a telecommunication network, and a remote device adapted to communicate with the external device through the telecommunication network.

19. The system of claim 18, wherein external system comprises a user interface configured to present one or more of the measured battery status trend and the calculated battery status trend.

20. The system of claim 19, wherein the remote device comprises a portion of the user interface.

21. A system for monitoring status of a battery in an implantable medical device, the system comprising:
a battery analyzer configured to analyze the status of the battery, the battery analyzer including:
a trending module including:
a parameter input configured to receive measured values of a battery functional parameter and calculated values of the battery functional parameter, the battery functional parameter indicative of a state of depletion of the battery, the measured values each indicative of an actual state of depletion of the battery, the calculated values each indicative of an expected state of depletion of the battery; and
a processing circuit configured to produce a measured battery status trend being a trend of the measured values of the battery functional parameter and a calculated battery status trend being a trend of the calculated values of the battery functional parameter; and
a trend alarm coupled to the trending module and configured to produce an alert signal when the measured battery status trend deviates from the calculated battery status trend by at least a specified performance margin for a monitoring period.

22. The system of claim 21, wherein the trend alarm is configured to produce the alert signal when a rate of change of the measured battery status trend deviates from a rate of change of the calculated battery status trend by at least a specified performance rate margin for the monitoring period.

23. The system of claim 21, comprising:
a battery parameter monitor configured to measure the battery functional parameter and produce the measured values of the battery functional parameter; and
a battery parameter calculator configured to produce the calculated values of the battery functional parameter each as a function of one or more specification parameters of the battery and one or more consumption parameters indicative of energy consumption from the battery.

24. The system of claim 23, wherein the battery parameter monitor comprises a terminal voltage monitor configured to measure a terminal voltage being a voltage across terminals of the battery.

25. The system of claim 23, wherein the battery parameter monitor comprises a charging time monitor configured to measure a capacitor charging time being a time interval during which a capacitor in the implantable medical device is charged to a specified energy level using the battery.

26. The system of claim 23, wherein the battery parameter monitor comprises a charge depletion monitor configured to produce a charge depletion parameter indicative of a cumulative charge depleted from the battery.

* * * * *

UNITED STATES PATENT AND TRADEMARK OFFICE
CERTIFICATE OF CORRECTION

| | |
|---|---|
| PATENT NO. | : 7,941,220 B2 |
| APPLICATION NO. | : 11/759400 |
| DATED | : May 10, 2011 |
| INVENTOR(S) | : Kenneth Tobacman |

It is certified that error appears in the above-identified patent and that said Letters Patent is hereby corrected as shown below:

On Sheet 4 of 10, in Figure 5, line 12, delete "REI" and insert -- ERI --, therefor.

Signed and Sealed this
Twelfth Day of July, 2011

David J. Kappos
*Director of the United States Patent and Trademark Office*